(12) United States Patent
Tu

(10) Patent No.: US 11,065,394 B2
(45) Date of Patent: Jul. 20, 2021

(54) SYRINGE WITH RETRACTABLE NEEDLE

(71) Applicant: GUANGDONG INTMED MEDICAL APPLIANCE CO., LTD, Foshan (CN)

(72) Inventor: Kewang Tu, Foshan (CN)

(73) Assignee: GUANGDONG INTMED MEDICAL APPLIANCE CO., LTD., Guangdong (CN)

( * ) Notice: Subject to any disclaimer, the term of this patent is extended or adjusted under 35 U.S.C. 154(b) by 36 days.

(21) Appl. No.: 15/744,171

(22) PCT Filed: Jul. 15, 2015

(86) PCT No.: PCT/EP2015/066171
§ 371 (c)(1),
(2) Date: Jan. 12, 2018

(87) PCT Pub. No.: WO2017/008850
PCT Pub. Date: Jan. 19, 2017

(65) Prior Publication Data
US 2018/0236179 A1 Aug. 23, 2018

(51) Int. Cl.
*A61M 5/32* (2006.01)
*A61M 5/50* (2006.01)
(Continued)

(52) U.S. Cl.
CPC .......... *A61M 5/3234* (2013.01); *A61M 5/322* (2013.01); *A61M 5/3221* (2013.01);
(Continued)

(58) Field of Classification Search
CPC ...... A61M 5/322; A61M 5/3221; A61M 5/50; A61M 5/502; A61M 5/347; A61M 5/3232;
(Continued)

(56) References Cited

U.S. PATENT DOCUMENTS 5,632,733 A 5/1997 Shaw
6,090,077 A 7/2000 Shaw
(Continued)

FOREIGN PATENT DOCUMENTS

CN 102 824 672 A 12/2012
CN 102824672 B * 6/2014
(Continued)

OTHER PUBLICATIONS

Global Spec, Wayback Machine, (https://web.archive.org/web/20150101000000*/https://www.acxesspring.com/coil-spring-design-basics.html) (Year: 2014).*
(Continued)

*Primary Examiner* — Laura A Bouchelle
*Assistant Examiner* — Anh Bui
(74) *Attorney, Agent, or Firm* — Collard & Roe, P.C.

(57) ABSTRACT

The invention relates to a syringe with a retractable needle comprising a barrel (2) having a nozzle (19) integrated in a male Luer adapter element (26); a piston (3) slidably arranged in the barrel (2) and coupled to a sealing element (16), said sealing element (16) having a central channel (20); a needle assembly comprising a needle (4), a needle holder (6) and a female Luer adapter element (7); a spring assembly arranged in the piston (3) comprising a spring sleeve (12), a spring (13) mounted on the spring sleeve (12), a spring tensioning element (14) located on the spring sleeve (12) and held in position by the piston wall, and a plunger (15) mounted within the spring sleeve; and a piston cap (10); said piston (3) being coupled to the sealing element (16) by means of the spring tensioning element (14); said spring sleeve (12) being held in position within the piston (3) by a ring element (18) protruding from the inner wall of the piston (3) and supporting the proximal end of the spring sleeve (12), the spring sleeve extending into the channel (20)
(Continued)

of the sealing element (16) to the distal end thereof; said spring sleeve (12) comprising at its distal end a circular protrusion (21) on the inside designed to engage a circular recess (22) at the proximal end of the needle holder (6); wherein the piston (3) comprises a holding ring (11) on its inner surface designed to engage with an outer flange (17) of the spring sleeve (12) after actuation of the spring (13).

10 Claims, 3 Drawing Sheets

(51) Int. Cl.
- *A61M 5/34* (2006.01)
- *A61M 5/315* (2006.01)
- *A61M 5/31* (2006.01)

(52) U.S. Cl.
CPC .......... *A61M 5/3232* (2013.01); *A61M 5/347* (2013.01); *A61M 5/502* (2013.01); A61M 2005/3104 (2013.01); A61M 2005/31508 (2013.01); A61M 2005/323 (2013.01); A61M 2005/3206 (2013.01); A61M 2005/3223 (2013.01); A61M 2005/3224 (2013.01); A61M 2005/3231 (2013.01); A61M 2005/3239 (2013.01); A61M 2005/3241 (2013.01)

(58) Field of Classification Search
CPC .......... A61M 5/3234; A61M 2005/323; A61M 2005/3231; A61M 2005/3206; A61M 2005/31508; A61M 2005/3224; A61M 2005/3223; A61M 2005/3104; A61M 2005/3239

See application file for complete search history.

(56) References Cited

U.S. PATENT DOCUMENTS

| 7,351,224 | B1 | 4/2008 | Shaw |
| 8,636,688 | B2 | 1/2014 | Shaw |
| 2008/0140005 | A1* | 6/2008 | Luo .................... A61M 5/3234 604/110 |

FOREIGN PATENT DOCUMENTS

| EP | 0 520 930 A1 | 12/1992 |
| JP | 2007315425 A * | 12/2007 |
| WO | 2007/101090 A2 | 9/2007 |
| WO | 2008/106712 A1 | 9/2008 |
| WO | 2011/127751 A1 | 10/2011 |

OTHER PUBLICATIONS

Tu,K., CN102824672B machine translation, Google Patents (Year: 2014).*

International Search Report of PCT/EP2015/066171, dated Mar. 14, 2016.

Written Opinion of the International Search Authority in PCT/EP2015/066171.

* cited by examiner

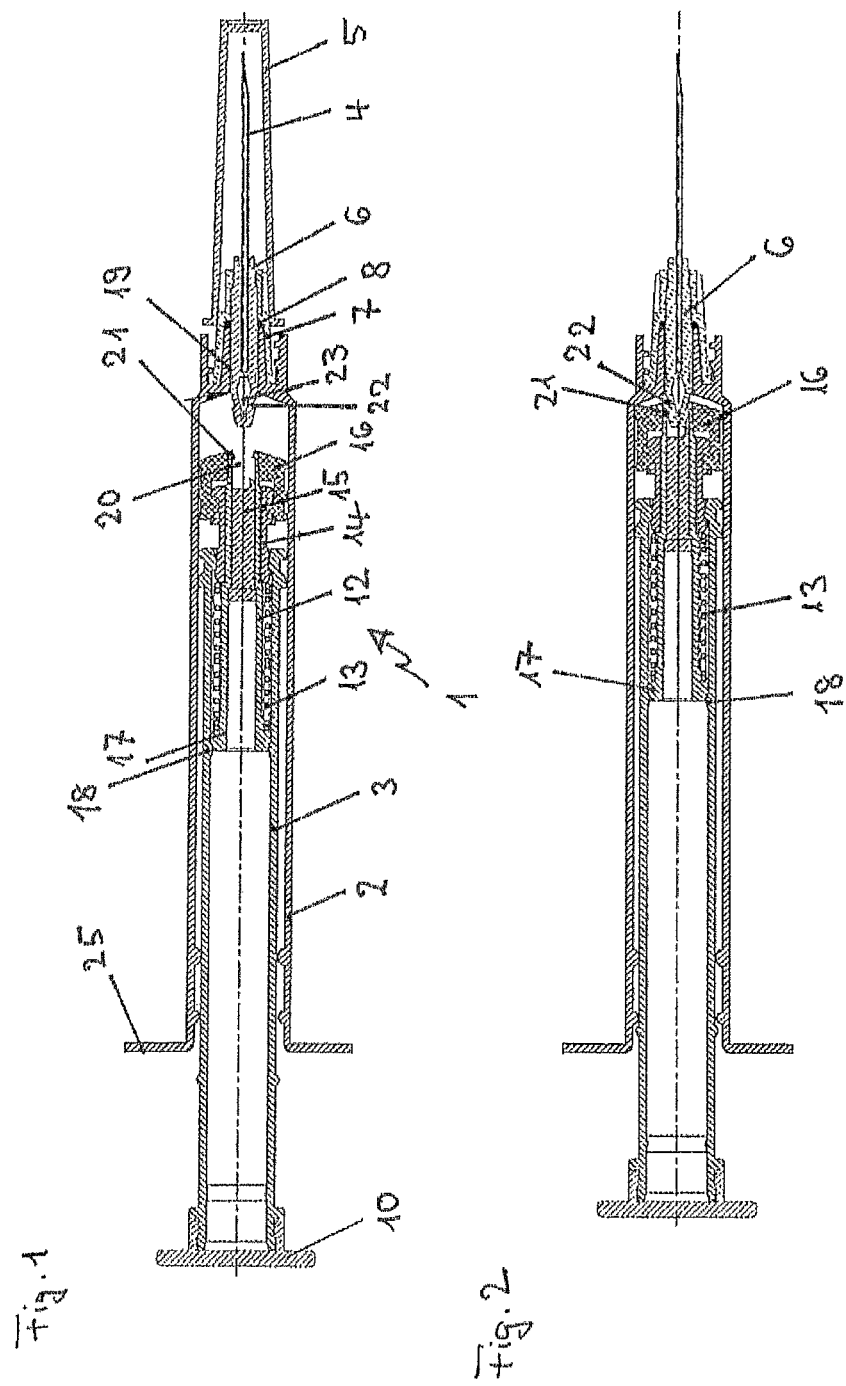

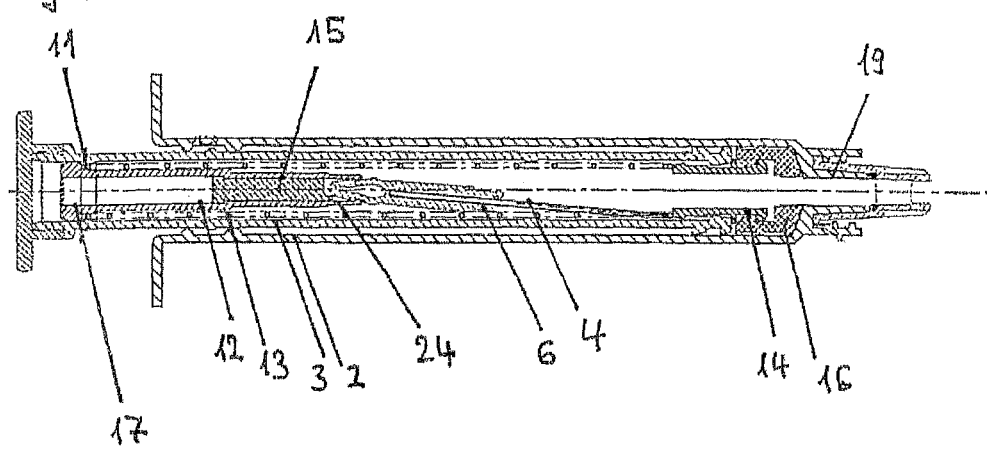
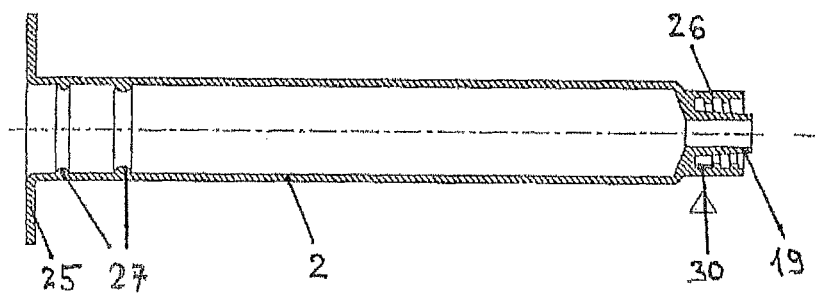
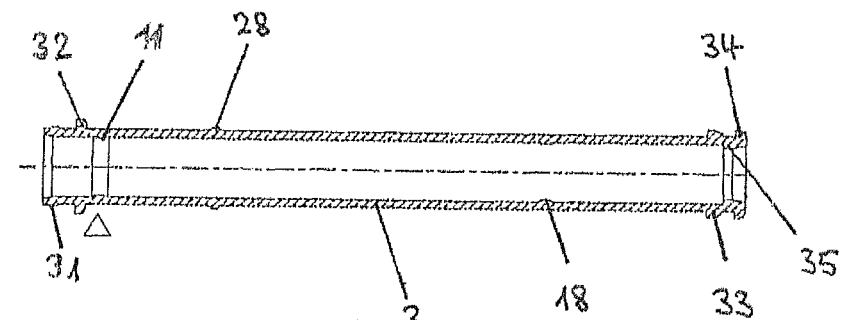
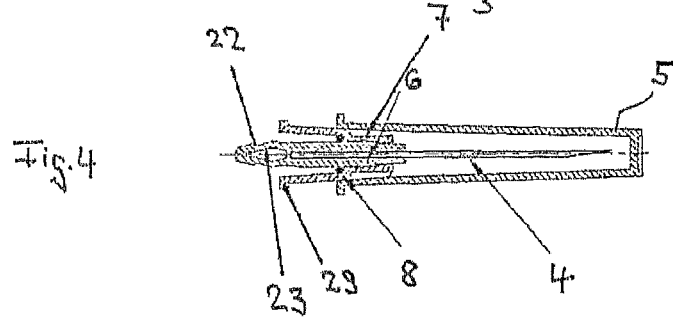

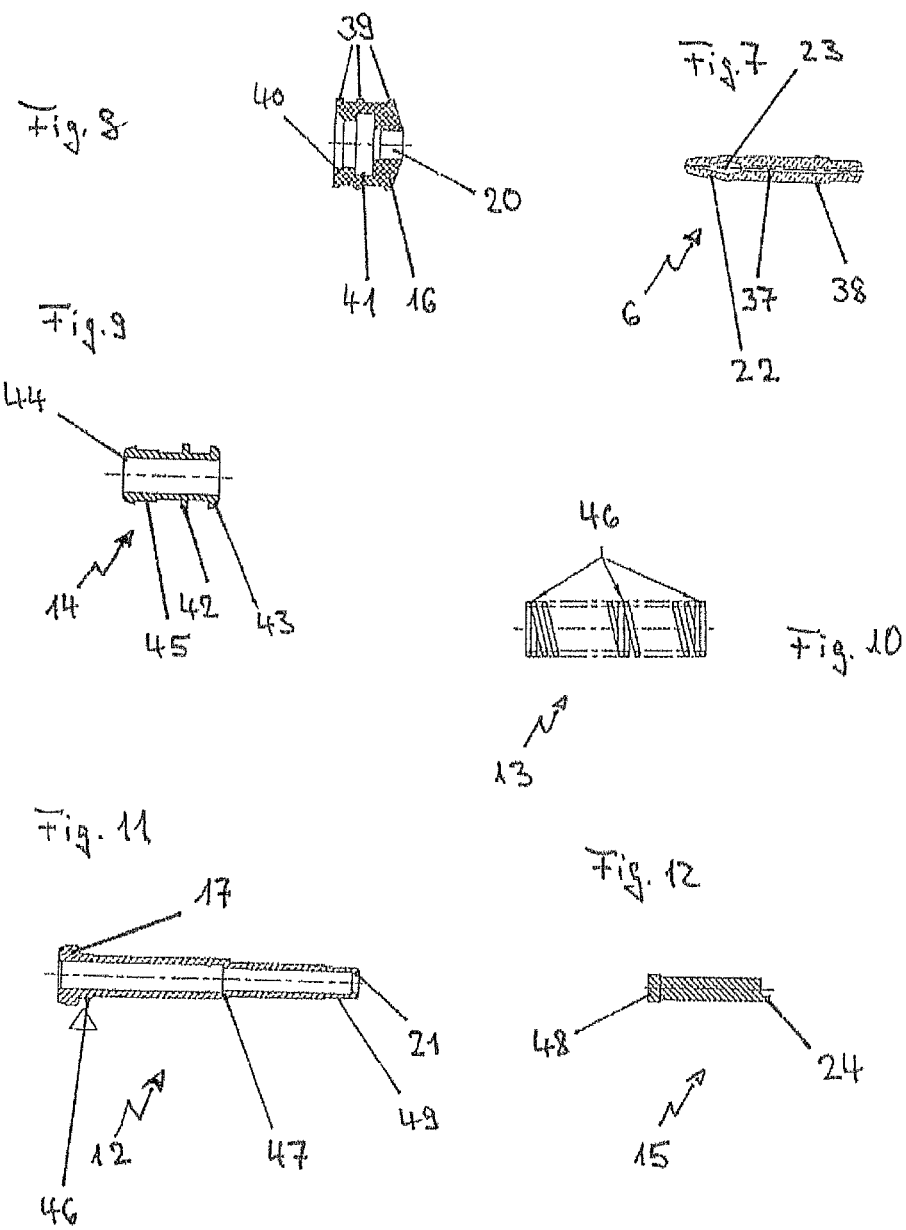

SYRINGE WITH RETRACTABLE NEEDLE

CROSS REFERENCE TO RELATED APPLICATIONS

This application is the National Stage of PCT/EP2015/066171 filed on Jul. 15, 2015, the disclosure of which is incorporated by reference. The international application under PCT article 21(2) was published in English.

The invention relates to a syringe with a retractable needle comprising
a barrel having a nozzle integrated in a male Luer adapter element;
a piston slidably arranged in the barrel and coupled to a sealing element, said sealing element having a central channel;
a needle assembly comprising a needle, a needle holder and a female Luer adapter element;
a spring assembly arranged in the piston comprising a spring sleeve, a spring mounted on the spring sleeve, a spring tensioning element slidably located on the spring sleeve and held in position by the piston wall, and a plunger mounted within the spring sleeve;
and a piston cap;
said piston being coupled to the sealing element by means of the spring tensioning element;
said spring sleeve being held in position within the piston by a ring element protruding from the inner wall of the piston and supporting the proximal end of the spring sleeve, the spring sleeve extending into the channel of the sealing element to the distal end thereof;
said spring sleeve comprising at its distal end a circular protrusion on the inside designed to engage a circular recess at the proximal end of the needle holder;
wherein upon exertion of pressure to the piston in its advanced position results in the engagement of the spring sleeve and the needle holder and the release of the spring sleeve thus actuating the spring and retracting the needle holder and the needle.

One way syringes are known in the art and have been developed for safety reasons, i.e. to avoid reuse of a syringe which might be contaminated after use with an infected patient, and to avoid accidental injury of a person coming into contact with a used exposed needle/syringe after injection procedure, prior to disposal. One approved way to render syringes non-reusable is to include a retraction mechanism for the needle, i.e. after injection, the needle is retracted into the syringe. This normally requires a spring mechanism and an actuator which upon actuation retracts the needle holder with a needle.

Syringes with retractable needles have been described in a number of U.S. patents, among others U.S. Pat. Nos. 5,632,733; 6,090,077; 7,351,224 and 8,636,688. All these patents describe syringes, where the spring mechanism is arranged in the distal part (nose) of the barrel. This arrangement has certain disadvantages, namely increase of sealing problems and space consumption by the retraction mechanism.

From CN 102 824 672 A a syringe with a retractable needle is known, which largely corresponds to the present syringe, as described above, but has certain problems with the locking of the needle within the Luer adapter and, after retraction, within the syringe. The compression spring used in this device has a tendency to tilt due to an insufficient guidance and support.

Thus, the underlying problem is to improve the syringe disclosed in CN 102 824 672 with regard to the mounting and securing of the needle at and within the syringe and the performance of the spring element.

Accordingly, the present invention relates to a syringe, as referenced above wherein in the introductory part, which is characterized by a piston comprising a holding ring on its inner surface is designed to engage an outer flange of the spring sleeve after actuation of the spring.

Moreover, the needle holder comprises a circular protrusion in its distal section to secure the needle holder within the male Luer adapter element.

The spring element comprises a compression spring with at least one ring element at the ends and preferably two adjacent ring elements at each end and in the middle section, the ring elements running perpendicular to the centerline of the spring.

In the subsequent description the term "distal" refers to the needle end of the syringe, and the term "proximal" to the handle end.

The present syringe comprises a barrel, a piston and a needle assembly. The barrel is a typical syringe barrel in cylinder form with a nose or nozzle at the distal end and a Luer threading surrounding the nozzle. Preferably, the nozzle is a male Luer cone integrated into the threading (Luer lock).

Within the barrel, a piston is slidably arranged and coupled to a sealing element, which may be formed by a rubber element or plastic element with rubber-elastic properties. The sealing element seals against the barrel wall and has a central channel. The sealing element is connected to the piston by means of a connector, which at the same time serves as a spring tensioning element.

The piston houses a spring assembly which comprises a spring sleeve, a spring mounted on the spring sleeve, the spring tensioning element located on the spring sleeve and held in position by the piston wall, and a plunger mounted within the spring sleeve. The spring sleeve is a tubular element with a flange protruding outwardly at the proximal end and extending into the channel of the sealing element, and ending with the distal outlet off the channel. The proximal flange of the spring sleeve support the spring at its proximal end. The proximal end of the spring tensioning element serves as a counter bearing of the spring, thus holding the spring under tension before actuation of the retraction mechanism.

The spring sleeve abuts with its proximal end against a flat ring provided at the inner wall of the piston so that it is held in position, unless pressure exercised on the piston forces the spring sleeve to pass over this ring.

The tensioning element located on the spring sleeve close to its distal portion is held in position by the distal end of the piston, which comprises two protruding rings outer, the recess between the rings cooperating with a corresponding protrusion on the spring tensioning element.

The syringe needle is part of the needle assembly, which comprises the needle, the needle holder and a female Luer adapter, preferably a female Luer lock part. The needle holder is a tubular element into which the needle is inserted with which its proximal end and to which the needle is secured, preferably by means of an adhesive. The needle holder has a proximal end, which is open to allow fluid content of the syringe to enter the needle and be injected into a patient. At the proximal end of the needle holder there is provided a circular recess for engagement of the retracting device, i.e. the distal end of the spring sleeve.

The needle holder is inserted into a female Luer adapter element and secured therein by friction. In order to improve the seat and to avoid the premature separation from the Luer adapter, the needle has, in the region close to the distal end, a circular protusion or ring, which is compressed by mounting the needle holder into the Luer adapter element. The female Luer adapter or Luer lock of the needle assembly is connected part in a conventional way to the male Luer adapter or lock of the barrel.

The piston of the syringe of the invention houses the spring assembly or retraction mechanism, which comprises a spring sleeve, a spring mounted on the spring sleeve, a spring tensioning element slidably located on the spring sleeve and a plunger mounted within the spring sleeve. The spring sleeve is secured at the inner wall of the piston, as described above. The spring, normally a compression spring, surrounds the spring sleeve and is held in its compressed state between a flange at the proximal end of the spring sleeve and the proximal end of the spring tensioning element. The spring is guided between the outer wall of the spring sleeve and the inner wall of the piston.

The spring tensioning element surrounds the spring sleeve in its distal portion and is held in tight contact with the spring sleeve by protrusions of the piston at the distal end thereof, which engage with corresponding elements at the proximal end of the spring tensioning element.

The plunger arranged within the distal portion of the spring sleeve and secured therein with an outer flange between a step of the spring sleeve and a holding ring. The plunger also serves as an additional sealing element to prevent contents of the syringe to flow into the piston.

The piston is closed by means of a conventional cap.

The sealing element is coupled to the piston by means of the spring tensioning element, which has circular protrusions at the distal and proximal ends which engage with corresponding recesses at the sealing element and the piston. In particular, the spring tensioning element extends with its distal part into the channel of the sealing element for engagement.

The spring sleeve also extends into the channel of the sealing element and ends with the channel so that upon contact of the sealing element with the distal end of the barrel the spring sleeve engages the recess at the proximal end of the needle holder. For this engagement, the spring sleeve has a flange or ring protruding from the inner wall at the distal end thereof.

During Operation of the syringe, the spring is under tension and allows the syringe to be filled through the needle and to be emptied through the needle. Only upon complete emptying of the barrel, the retraction mechanism is actuated, first causing a coupling of the spring sleeve to the needle holder and thereafter, upon further insertion of the piston under compression of the sealing element, releasing of the spring sleeve from the holding ring at the piston and actuating of the spring. The needle holder with the needle coupled to the spring sleeve is withdrawn into the barrel and the piston of the syringe.

The expansion of the spring also causes the spring sleeve to pass with its proximal end a holding ring in the proximal part of the piston, where the retraction mechanism stays locked. This prevents the retraction mechanism to return to the distal part of the syringe which might result in a re-appearance of the needle through the nozzle and Luer lock, which might cause injury to a person and possibly infection of this person.

The material of the syringe parts is mostly conventional, preferably a plastic material, such as polypropylene. The sealing element may be made from a rubber material or a plastic material having rubber-like properties, such as a thermos plastic elastomer. Spring and needle are made from conventional spring and medical steel.

The invention is further explained by means of the attached drawings showing in sectional view:

FIG. 1 a syringe of the invention ready for operation;

FIG. 2 the syringe of FIG. 1 immediately before actuation;

FIG. 3 the syringe of FIG. 1 after actuation of the retraction mechanism;

FIG. 4 the needle assembly of the syringe of FIG. 1

FIG. 5 the barrel;

FIG. 6 the piston;

FIG. 7 the needle holder;

FIG. 8 the sealing element;

FIG. 9 the spring tensioning element;

FIG. 10 the spring;

FIG. 11 the spring sleeve; and

FIG. 12 the plunger of the syringe of FIG. 1.

FIG. 1 shows a syringe according to the present invention before use. Syringe 1 comprises barrel 2, piston 3, needle 4 and piston cap 10. Needle 4 is inserted and adhesively secured in needle holder 6, which itself is inserted into nozzle 19 of barrel 1. The proximal end of needle holder 6 is located in the distal region of barrel 1, thus been available for coupling to the retraction mechanism.

Needle holder 6 is attached to nozzle 19 by means of the female part 7 of a Luer-lock, nozzle 19 serving as the male counterpart.

Piston 3 houses spring sleeve 12, which is surrounded by compression spring 13. Spring sleeve 12 has a proximal flange 17 which serves to support spring sleeve 12 against ring element 18 protruding from the inside wall of piston 3. Flange 17 at the same time is the proximal support for spring 13 which at its distal end is supported by the proximal end of spring tensioning element 14. Spring tensioning element 14 is secured at its proximal end at the inside of piston 3 and at its distal end in a channel with sealing element 16, thus coupling piston 3 and sealing element 16. Within the distal region of spring sleeve 12 plunger 15 is arranged which completes the sealing of the syringe chamber of barrel 2.

Sealing element 16 has a central channel 20 which is lined by the distal part of spring sleeve 12. Spring sleeve 12 has an inner flange 21 which serves as a complying element and is designed to couple to the proximal end of needle holder 6, i.e. to the circular recess 22 close to the proximal end. Numeral 23 designates the access opening to needle 4 in the form of a through hole perpendicular to the axis of needle holder 6.

FIG. 2 shows the syringe of FIG. 1 after injection of its contents. The state shown is before activation of retraction, but after coupling of the retraction mechanism to the needle holder 6 through spring sleeve 12. Spring sleeve 12 is still in its secured state at holding ring 18 of piston 3. On the other hand, sealing element 16 has almost reached its final position in barrel 2. A further insertion of piston 3 would release spring sleeve 12 with spring 13 and cause retraction of the needle.

FIG. 3 shows the syringe of FIGS. 1 and 2 after actuation of the retraction mechanism. Needle holder 6 with needle 4 have been withdrawn into piston 3, the proximal end of needle holder 6 being inserted into the distal end of spring sleeve 12. Spring 13 is shown in the expanded state, spring sleeve 12 in its proximal position with its flange 17 close to the proximal end of piston 3. Flange 17 has passed over holding ring 11 on the inner wall of piston 12 and is thus blocked and prohibited to again move in direction of nozzle 19. Holding ring 11 has a flat design so that it may be easily passed by flange 17 under pressure of spring 13, but safely retains spring sleeve 12, when no reverse pressure is applied.

FIG. 4 shows the spring assembly ready for insertion into Luer-lock at element 19 the distal part of barrel 2. The spring assembly is protected by sheath 5 which is frictionally attached to female part 7 of the Luer-adapter. Inside the couple sheath is needle 4 which is inserted into needle holder 6. At the proximal end of needle holder 6 there is an open passage way 23 which allows contents of the syringe to enter into the needle upon actuation of the piston. Recess 22 at the proximal end of needle holder 6 is designed to be coupled to the spring retraction mechanism located in piston 3.

The needle assembly comprises a sealing ring 8 which is located at a step of the female part 7 of the Luerlock and is designed to cooperate with the front end of the male part 19 of the Luerlock at the distal end of barrel 2.

FIG. 5 shows barrel 2 with the male part 19 of the Luer-lock at its distal end. At the proximal end a handle 25 facilitates operation of the syringe. Two stopper rings 27 at the proximal end cooperate with a circular protrusion 28 on piston 3, the proximal one defining the piston position after release of the syringe contents and the distal ring 27 defining the piston position for release of the spring and retraction mechanism.

Male part 19 of the Luerlock is surrounded by a threading 26 which cooperates with a corresponding flange 29 at the distal end of the female part 7 of the Luer-adapter.

Within the threading of the Luerlock, a pad 30 attached to the outer wall in the proximal winding of the Luerlock threading serves to block female part 7 of the Luer-lock in position and at the same time tightens the lock between Luer-lock part 7 and needle holder 6, see below (FIG. 7).

FIG. 6 shows piston 3 with two circular protrusions 31 and 32 at the proximal end which secure cap 10. In a protrusion 11 is a stopper ring which serves to secure retracted spring sleeve 12. Stopper ring 28 cooperates with Stopper rings 27 at the inside of barrel 2 defining piston positions before and after release of the retraction mechanism, as discussed above. Inner ring 18 is a stoppering for spring sleeve 12, flange 17 of the spring sleeve 12 being supported on ring 18 on the distal side thereof. Outer circular protrusions 33 and 34. An inner ledge 35 cooperates with a corresponding recess 36 on spring tensioning element 14.

FIG. 7 shows needle holder 6 with a central channel 37 housing needle 4, a recess 22 at the proximal end, a throughhole 23 open to channel 37 through which the syringe content can pass into channel 37 and the needle arranged therein and a circular ring 38 which serves to improve the seat of needle holder 6 within the female part 7 of the Luer-adapter. Ring 38 may cooperate with a circular recess within Luerpart 7.

FIG. 8 shows the sealing element 16 with its central channel 20, outer ribs 39 which seal against the inner wall of barrel 2, and a conical flange 40 and a circular recess 41 to accommodate a corresponding profile on spring tensioning element 14.

FIG. 9 shows spring tensioning element 14, which is of tubular shape and has at its distal end two circular protrusions 42 and 43 which allow engagement with sealing element 16, see flange 40 and recess 41 at the inside. At the proximal end of spring tensioning element 14 a flange 44 supports the distal end of spring 13. A widened part 45 of the wall of spring tensioning element 14, which however does not protrude as far as flange 44, serves as the seat of ring element 35 of the distal end of piston 3.

FIG. 10 shows schematically spring 13 with its two ends and the middle section, where spring windings from parallel double rings 46 running almost perpendicular to the center line of spring 13.

FIG. 11 shows spring sleeve 12, which is of tubular shape with the diameter narrowing from proximal to distal. At the proximal end flange 17 is designed to pass holding ring 11 at the inner wall of piston 3.

Adjacent to flange 17, spring sleeve 12 has a widened section 46 which serves as a seat and holding element for spring 13. Spring 13, with its proximal end, is supported by the distal side of flange 17 on one side and by flange 44 of spring tensioning element 14, at the other side.

Spring sleeve 12 has in its middle section a step 47 with a distal section of reduced diameter. Step 47 serves as a support of flange 48 of plunger 15, see FIG. 12. Moreover, at the distal end, a section with a reduced outer diameter 49 corresponds to the inner diameter of channel 20 at the distal end of sealing element 16. The distal end of spring sleeve 12 is provided with a circular protrusion 21 which is designed to engage with recess 22 at the proximal end of needle holder 6. Spring sleeve 12, when mounted, ends with channel 20 at the distal end of sealing element 16.

FIG. 12 shows plunger 15 with flange 48 at its distal end and a distal nose 24 having a hook like shape, which, after retraction of needle holder 6 with needle 4, is suited to tilt the needle holder within piston 3. The tilting of needle holder 6 and needle 4 in its retracted position helps to prevent them to pass through the nozzle to the outside and to cause injury.

The above drawings all are sectional drawings showing a preferred embodiment of the syringe of the invention. It is selfunderstanding that not all features shown in the drawings are necessary to provide a working syringe with a rejectable needle under the present claims.

The invention claimed is:

1. Syringe with a retractable needle comprising
   a barrel (2) having a nozzle (19) integrated in a male Luer adapter element;
   a piston (3) slidably arranged in the barrel (2) and coupled to a sealing element (16), said sealing element (16) having a central channel (20);
   a needle assembly comprising a needle (4), a needle holder (6) and a female Luer adapter element (7);
   a spring assembly arranged in the piston (3) comprising a spring sleeve (12), a spring (13) mounted on the spring sleeve (12), a spring tensioning element (14) located on the spring sleeve (12) and held in position by the piston wall, and a plunger (15) mounted within the spring sleeve (12); and
   a piston cap (10);
   said piston (3) being coupled to the sealing element (16) by means of the spring tensioning element (14);
   said spring sleeve (12) being held in position within the piston (3) by a ring element (18) protruding from the inner wall of the piston (3) and supporting the proximal end of the spring sleeve (12), the spring sleeve (12) extending into the channel (20) of the sealing element (16) to the distal end thereof;
   said spring sleeve (12) comprising at its distal end a circular protrusion (21) on the inside designed to engage a circular recess (22) at the proximal end of the needle holder (6);
   wherein the spring sleeve (12) comprises an outer flange (17) supporting the proximal end of the spring (13) and comprises a widened section (46a) adjacent to the outer flange (17) for securing the proximal end of the spring (13);

wherein upon exertion of pressure to the piston (3) in its advanced position results in the engagement of the spring sleeve (12) and the needle holder and the release of the spring (13) sleeve thus actuating the spring and retracting the needle holder (6) and the needle (4), wherein the piston (3) comprises a holding ring (11) on its inner surface in the proximal part of the piston;

wherein the holding ring is designed to engage with the outer flange (17) of the spring sleeve (12) where, after actuation of the spring (13) the reaction mechanism stays locked; and wherein the spring element (13) is a compression spring comprising closed ring elements at the ends where spring windings form parallel double rings (46) that run perpendicular to the centerline of the spring (13) and are seated on and held by the widened section.

2. The syringe of claim 1, wherein the needle holder comprises a circular protrusion (38) in its distal section to secure the needle holder (6) within the female Luer adapter element (7).

3. The syringe of claim 1, wherein the spring element comprises two adjacent ring elements (46) at each end and in the middle section.

4. The syringe of claim 1, wherein said outer flange (17) of the spring sleeve (12) is the flange supporting the proximal end of the spring sleeve (12) against the ring element (18) protruding from the inner piston wall.

5. The syringe of claim 1, wherein the holding ring (11) is located near the proximal end of the piston (3).

6. The syringe of claim 1, wherein the sealing element (16) is made from rubber or a plastic material having rubber-like properties.

7. The syringe of claim 6, wherein the sealing element (16) is compressible.

8. The syringe of claim 1, wherein the needle assembly comprises a sealing ring (8).

9. The syringe of claim 2, wherein the circular protrusion (38) at the needle holder (6) is designed to secure the needle holder (6) within the female Luer adapter element (7), by friction.

10. The syringe of claim 7, wherein spring actuation is effected after engagement of the spring sleeve (12) with the proximal end of the needle holder (6).

* * * * *